United States Patent [19]

Pan et al.

[11] Patent Number: 4,980,505

[45] Date of Patent: Dec. 25, 1990

[54] ORGANIC SYNTHESIS

[75] Inventors: Yuh-Guo Pan, Stamford; Lana L. Hochman, Fairfield, both of Conn.

[73] Assignee: Clairol Incorporated, New York, N.Y.

[21] Appl. No.: 285,906

[22] Filed: Dec. 16, 1988

[51] Int. Cl.$^5$ .................. C07C 37/045; C07C 209/00

[52] U.S. Cl. ............................ 564/414; 564/390; 564/443; 568/767

[58] Field of Search ............. 564/390, 391, 414, 443, 564/389; 568/769

[56] References Cited

U.S. PATENT DOCUMENTS

| | | | |
|---|---|---|---|
| 2,194,215 | 3/1940 | Bruson et al. | 564/390 X |
| 3,187,049 | 6/1965 | Green | 564/390 X |
| 3,188,346 | 6/1965 | Kallopissis et al. | 564/414 |
| 3,461,172 | 8/1969 | Previc | 564/390 X |
| 3,592,854 | 7/1971 | Potts et al. | 564/414 X |
| 3,946,086 | 3/1976 | Borisovid et al. | 360/624 X |
| 4,302,599 | 11/1981 | Peer et al. | 564/414 X |
| 4,475,001 | 10/1984 | Lester | 568/784 |
| 4,480,140 | 10/1984 | Lester | 568/784 |

OTHER PUBLICATIONS

"An Efficient Synthesis of 3,5-Dihydroxy-4-methylbenzoic Acid", R. Borchardt, *J. Org. Chem.*, (1981), 46, pp. 5021-5022.

"Catalytic Hydrogenation over Platinum Metals", P. N. Rylander, (1967), *Academic Press*, pp. 467 & 498.

"Advances in the Chemistry of Mannich Bases", *Synthesis*, (1973), pp. 749-750.

*Primary Examiner*—Robert V. Hines
*Attorney, Agent, or Firm*—S. Nolan

[57] ABSTRACT

The conversion of ortho-hydroxylated Mannich bases to the corresponding methylated compounds, e.g., cresols, can be effectively carried out using a novel hydrogenation technique.

9 Claims, No Drawings

ORGANIC SYNTHESIS

BACKGROUND

The with the cleavage of ortho-hydroxylated aromatic Mannich bases to yield methylated products of relatively high purity using only moderate reaction conditions.

The ortho-hydroxylated aromatic Mannich bases derived from dimethylamine were stable under catalytic hydrogenation conditions, whereas the corresponding morpholino derivatives were able to achieve hydrogenolysis. P. N. Rylander reported this in "Catalytic Hydrogenation Over Platinum Metals", Academic Press (1967) at page 467. Green et al, in U.S. Pat. No. 3,187,049 (1965) showed that when the Mannich base has a nitro group meta to the aminomethyl group, the nitro group can be reduced and the dimethylamino group of the hydrochloride salt can be cleaved to give the methyl group in one operation using 33% by weight of 10% Pd on barium sulfate (3.3% Pd by weight) as catalyst. The absence of intramolecular hydrogen bonding in the hydrochloride salt was responsible for the ease of hydrogenolysis of the dimethylamino group. The poor reactivity of ortho-phenolic Mannich bases was discussed by M. Tramontini in "Advances in the Chemistry of Mannich Bases", Synthesis, volume 703 (1973), at page 750.

In U.S. Pat. No. 3,461,172, Previc disclosed the hydrogenation of ortho-phenolic Mannich bases via the steps of (1) conversion of the base to its hydrochloride salt and (2) hydrogenation of the salt using an acid resistant catalyst at 100 to 3,000 psi hydrogen pressure and 125° to 225° C.

R. Borchardt et al reported in J. Org. Chem., 46 (1981), pp. 5021-2 that a 70% yield of 3,5.-dihydroxy-4-methylbenzoic acid could be obtained from 2,6-dibromo-3,5-dihydroxy-4-[(N,N-dimethylamino)methyl]benzoic acid by treatment with 3N sodium hydroxide in an equal weight of Raney nickel alloy at 25°-30° C.

U.S. Pat. Nos. 3,946,086; 4,117,244; 4,215,229; and 4,480,140 disclose the hydrogenation of Mannich bases at temperatures above 80° C.

U.S. Pat. No. 4,475,001 discloses a process for producing ortho-alkylated phenols from phenols via the steps of (1) making a tertiary alkylated phenol, (2) making a Mannich base from the product of (1) while retaining the t-alkyl group, (3) removing the t-alkyl group, and (4) hydrogenating the Mannich base at 0° to 175° C. This synthesis, like that of Previc, involves the use of an intermediate.

THE INVENTION

Applicants have discovered that ortho-aminomethylated hydroxyaromatic compounds can be converted to the corresponding ortho-methylated derivatives via catalytic hydrogenation in alkaline media using mild temperatures and low to moderate hydrogen pressures.

In a preferred embodiment, 5-amino-o-cresol was produced by the hydrogenolysis of 5-acetamido-2-[(N,N-dimethylamino)methyl]-phenol. The hydrogenation occurred over 10% by weight of Pd/C catalyst (3% Pd content) in dilute KOH at about 30 psi hydrogen pressure and about 70° C. After adjusting the pH to about 12, 5-amino-o-cresol was obtained in about 70% yield.

ADVANTAGES

The process of this invention has several advantages over known techniques for producing ortho-alkylated hydroxyaromatic compounds. Energy requirements are lessened because relatively low temperatures are employed.

In addition, costs of operation are lower than in conventional processes because catalyst and hydrogen pressure needs are more easily met.

These advantages and other aspects of the invention will become apparent after a consideration of the following invention description.

DESCRIPTION OF THE INVENTION

The invention deals with a process for the production of ortho-methylated hydroxyaromatic compounds via the cleavage of the corresponding Mannich bases.

MANNICH BASES

The Mannich bases which can be converted in accordance with the invention include compounds of Formula I:

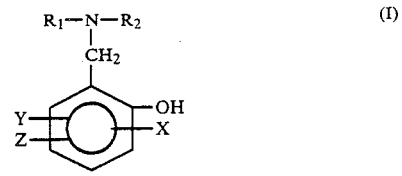

wherein X, Y, Z, $R_1$, and $R_2$ can each independently be: hydrogen, alkyl, nitro, amino, alkoxy, halogen, haloalkyl, nitroalkyl, aminoalkyl, aryl, acetamido, haloaryl, alkylaryl, alkoxyaryl; Y and Z may be members of a 5- or 6-membered carbocyclic or heterocyclic ring; $R_1$ and $R_2$ may be members, along with N, in a 5- or 6-membered nonaromatic or heterocyclic ring.

It is preferred that the Mannich bases conform to one of formulas II, III,

Formula II is:

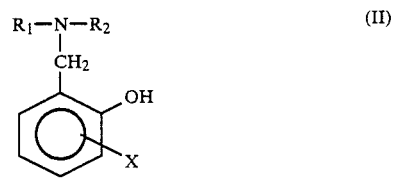

Wherein X, $R_1$ and $R_2$ are as defined above.

Formula III is:

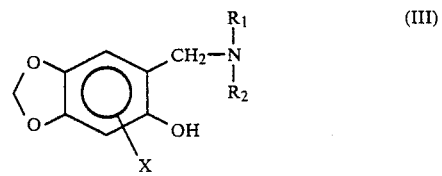

wherein X, $R_1$ and $R_2$ are as defined above.

Formula IV is:

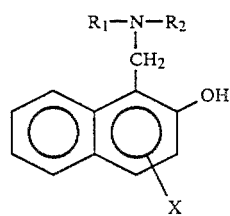

Formula V is:

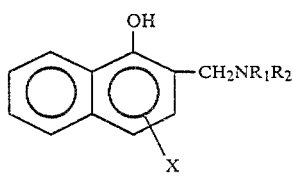

wherein X, R₁ and R₂ are as defined above.

Preferably, $R_1$ and $R_2$ are both methyl groups; X is hydrogen, nitro, amino or acetamido. Thus preferred Mannich bases for reaction herein are 5-acetamido-2-[(N,N-dimethylamino) methyl]phenol, 2-[(N,N-dimethylamino)methyl]-4,5-methylenedioxyphenol, 1-[(N,N-dimethylamino)methyl]-2-naphthol, and 2-[(N,N-dimethylamino)methyl1]-4-nitro-1-naphthol, and the like as shown in Table I. Mixtures are contemplated.

Some highly preferred Mannich bases, and the products which they yield are shown in Table I.

Table I: Typical Manich bases and products made therefrom

TABLE I

Typical Manich bases and products made therefrom

| Base | Product | |
|---|---|---|
| 2-[CH₂N(CH₃)₂]-phenol with HNAc | 2-methyl-phenol with NH₂ | A. |
| 2-[CH₂N(CH₃)₂]-phenol with NO₂ | 2-methyl-phenol with NH₂ | B. |
| 2-[CH₂N(CH₃)₂]-toluene with HNAc | 2-methyl-phenol with NH₂ | C. |
| 4,5-methylenedioxy-2-[CH₂N(CH₃)₂]-phenol | 4,5-methylenedioxy-2-methyl-phenol | D. |
| 1-[CH₃N(CH₃)₂]-2-naphthol | 1-methyl-2-naphthol | E. |
| 2-[CH₂N(CH₃)₂]-1-naphthol | 2-methyl-1-naphthol | F. |

TABLE I-continued

Typical Manich bases and products made therefrom

| Base | Product | |
|---|---|---|
| (structure with OH, CH₂N(CH₃)₂, HNAc on naphthalene) → | (structure with OH, CH₃, NH₂ on naphthalene) | G. |
| (structure with OH, CH₂N(CH₃)₂, NO₂ on naphthalene) → | (structure with OH, CH₃, CH₂ on naphthalene) | H. |

The method of production of the Mannich base reactant is not critical to the instant invention. Useful Mannich bases are derived from a variety of starting materials by techniques which are well known in the art. One preferred base, 5-acetamido-2-[(N,N-dimethylamino)-methyl]phenol is prepared by reacting a 1:1:1.2 molar mixture of 3-acetamidophenol, formaldehyde, and dimethylamine for about two hours at room temperature to give the desired product in about 70% yield (m.p. 158°–160° C.).

HYDROGENATION

The cleavage of the Mannich base is carried out via catalytic hydrogenation. The hydrogenation conditions used are significantly less severe than those customarily employed in the art.

Hydrogen pressures on the order of about 30 to about 75 psi, preferably about 50 to about 60 psi, are operable. Higher pressures may be used, but are not required, since hydrogen levels of 60 psi or less are generally adequate.

The catalyst employed during the bases' reaction with hydrogen is generally a metal, e.g., platinum or palladium, catalyst on a carbon or other suitable support. Other useful carriers or supports include barium sulfate. Palladium/carbon combinations are preferred. Other combinations are contemplated.

The quantity of palladium or other metal used in the combination will generally be about 0.1 to about 10 weight percent, preferably about 0.2 to about 5 weight percent, most preferably about 0.3 weight percent, based on the total weight of the metal/substrate ratio.

The solvent employed during reaction will generally comprise one or more neutral or alkaline materials in an aqueous or non-aqueous carrier. Suitable carriers include water, $C_{1-6}$ alcohol, e.g., ethanol, and mixtures thereof.

The alkaline agents, when used, are generally alkali or alkaline earth hydroxides. Alkali hydroxides are preferred. Potassium hydroxide is highly preferred.

Of the materials such as buffers, gaseous carriers, anti-oxidants, and the like may also be present, in suitable quantities, during the hydrogenation.

The level of potassium hydroxide or other alkaline agent, when employed, in the reaction solvent or carrier will be about 2 to about 10 molar equivalents, preferably about 3 to about 5 molar equivalents. Initial pH's of about 8 to about 14 are useful.

Time and temperature requirements for the cleavage procedure are generally moderate. Reaction times on the order of about 30 minutes to about 10 hours, preferably 2 to 3 hours are used.

Reaction temperatures may range from about ambient or room temperature to about 50° to 100° C., with temperatures of about 70° to about 80° C. preferred.

The type of reaction vessel employed is not critical. However, devices such as a Parr hydrogenation apparatus are useful.

RECOVERY TECHNIQUE

The pH of the final mixture, i.e., containing the desired product, may be adjusted before recovery is begun. Alkaline pH values of about 10 to about 14, preferably about 12, are used. Generally, the ortho-methylated products of the invention are recoverable from the reaction vessel by techniques such as filtration, extraction, and the like.

EXAMPLES

Example I

Synthesis of 5-amino-o-cresol from m-aminophenol (structure: phenol with NH₂) → (structure: phenol with HNCOCH₃) →

(structure: phenol with CH₂N(CH₃)₂ and HNCOCH₃) → (structure: cresol with CH₃ and NH₂)

Experimental Procedure:

Acetic anhydride (22.5 g; 220 mmol) was slowly added to a suspension of 24.0 g (220 mmol) of m-aminophenol in 60 g of crushed ice and 60 ml of cold water. The reaction mixture was vigorously stirred for 30 minutes. The white precititate was filtered, washed with cold water, and air-dried to give 30.5 g (92% yield) of pure 3-acetamidophenol.

To a solution of 30.5 g (202 mmol) of 3-acetamidophenol in 27.5 g (244 mmol) of 40% dimethylamine and 25 ml of methanol, was added 16.4 g (202 mmol) of 37% formalin. The reaction mixture was placed in an ice bath just after the precipitate formed (ABOUT 15 minutes). The white precipitate was filtered after 15–30 minutes, washed with cold water, and air-dried to give 28.0 g (67% yield) of 5-acetamido-2-[(N,N-dimethylamino)-methyl]phenol.

In the hydrogenolysis step, 8.0 g (38 mmol) of 5-acetamido-2-[(N,N-dimethylamino)methyl]phenol was dissolved in 54 ml (162 mmol) of 3N potassium hydroxide solution in a Parr bottle. Palladium on activated carbon (0.8 g; 3% Pd/C) was added to the solution. The reaction mixture was shaken under hydrogen on a Parr apparatus for 3 hours at 70°–80° C. and 60 psi. The catalyst (Pd/C) was removed by filtration and the filtrate brought to about pH 12 with 6M HCl (15–20 ml). The off-white crystalline product precipitated out of solution. The solution was cooled and the precipitate filtered, washed with water, and dried overnight in a vacuum oven to give 3.2 g (68% yield) of 5-amino-o-cresol, m.p. 158°–160° C.). The purity of 5-amino-o-cresol prepared by this procedure was determined to be 97% by perchloric acid titration.

Example II

Synthesis of 4-amino-o-cresol from 2-[(N,N-dimethylamino)-methyl]-4-nitrophenol.

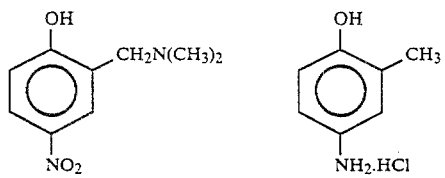

2-[(N,N-Dimethylamino)methyl]-4-nitrophenol (2.0 g; 10.1 mmol) was dissolved in a solution of 7 ml of 3N potassium hydroxide and 28 ml of water, then 0.20 g of palladium/ carbon (3% Pd content) was added. The reaction mixture was shaken under hydrogen on a Parr apparatus for 2 to 3 hours at about 70° C. The catalyst (Pd/C) was removed by filtration. Concentrated hydrochloric acid was added to the filtrate to precipitate out 4-amino-o-cresol hydrochloride which was filtered, washed with water and air-dried to give 0.8g (50% yield).

Reasonable variations, such as those which would occur to a skilled artisan, can be made herein without departing from the scope of the invention.

We claim:

1. A process for the synthesis of ortho-methylated hydroxyaromatic compounds consisting essentially of the steps of hydrogenolysis of an ortho-hydroxylated aromatic Mannich base using about 30 to about 60 psi of hydrogen pressure, in the presence of an aqueous alkaline solvent, and acid precipitation of the result ortho-methylated hydroxyaromatic compound.

2. The process of claim 1 wherein the Mannich base employed is at least one compound of formula I:

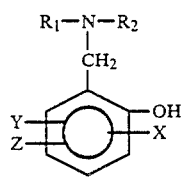

wherein X, Y, Z, $R_1$, and $R_2$ can each independently be: hydrogen, alkyl, nitro, amino, alkoxy, halogen, halcalkyl, nitroalkyl, aminoalkyl, aryl, acetamido, haloaryl, alkylaryl, alkoxyaryl; Y and Z may be members of a 5- or 6-membered carbocyclic or heterocyclic ring; $R_1$ and $R_2$ may be members, along with N, in a 5- or 6-membered nonaromatic or heterocyclic ring.

3. The process of claim 2 wherein the Mannich base is of formula II, III, IV or V:

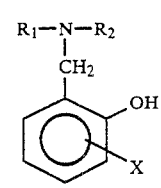

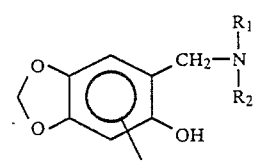

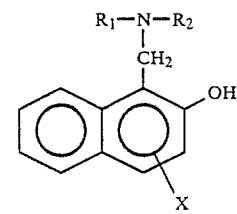

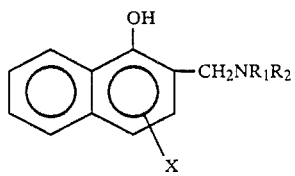

wherein X, $R_1$ and $R_2$ are as defined in claim 2.

4. The process of claim 3 wherein the Mannich base is 5-acetamido-2-[(N,N-dimethylamino)methyl]phenol.

5. The process of claim 4 wherein there is a catalyst present.

6. The process of claim 5 wherein the catalyst is a palladium/carbon catalyst.

7. The process of claim 6 wherein the solvent is aqueous potassium hydroxide.

8. The process of claim 2 wherein a temperature of 70° to 80° C. is employed.

9. The process of claim 7 wherein a temperature of 70° to 80° C. is employed.

* * * * *